United States Patent
Levinski et al.

(10) Patent No.: US 10,197,389 B2
(45) Date of Patent: Feb. 5, 2019

(54) APPROACHES IN FIRST ORDER SCATTEROMETRY OVERLAY BASED ON INTRODUCTION OF AUXILIARY ELECTROMAGNETIC FIELDS

(71) Applicant: KLA-Tencor Corporation, Milpitas, CA (US)

(72) Inventors: Vladimir Levinski, Migdal Ha'Emek (IL); Yuri Paskover, Caesarea (IL); Yuval Lubashevsky, Haifa (IL); Amnon Manassen, Haifa (IL)

(73) Assignee: KLA-Tencor Corporation, Milpitas, CA (US)

( * ) Notice: Subject to any disclaimer, the term of this patent is extended or adjusted under 35 U.S.C. 154(b) by 11 days.

(21) Appl. No.: 15/305,166

(22) PCT Filed: Aug. 18, 2016

(86) PCT No.: PCT/US2016/047619
§ 371 (c)(1),
(2) Date: Oct. 19, 2016

(87) PCT Pub. No.: WO2017/044283
PCT Pub. Date: Mar. 16, 2017

(65) Prior Publication Data
US 2017/0268869 A1 Sep. 21, 2017

Related U.S. Application Data

(60) Provisional application No. 62/215,895, filed on Sep. 9, 2015.

(51) Int. Cl.
*G01B 11/02* (2006.01)
*G01B 11/27* (2006.01)
(Continued)

(52) U.S. Cl.
CPC .......... *G01B 11/272* (2013.01); *G01B 9/0201* (2013.01); *G01N 21/4788* (2013.01); *G03F 7/70633* (2013.01)

(58) Field of Classification Search
CPC ................. G01B 9/0201; G01B 11/272; G01N 21/4788; G01N 15/0205; G01N 15/0211; G01N 15/0216; G03F 7/70633
(Continued)

(56) References Cited

U.S. PATENT DOCUMENTS

| 5,631,773 A | 5/1997 | Suzuki |
| 6,710,876 B1 | 3/2004 | Nikoonahad et al. |

(Continued)

FOREIGN PATENT DOCUMENTS

WO    2014062972    4/2014

OTHER PUBLICATIONS

ISA/KR, International Search Report for PCT/US2016/047619 dated Nov. 25, 2016.

*Primary Examiner* — Tarifur R Chowdhury
*Assistant Examiner* — Jonathon Cook
(74) *Attorney, Agent, or Firm* — Hodgson Russ LLP

(57) ABSTRACT

Metrology measurement methods and tools are provided, which illuminate a stationary diffractive target by a stationary illumination source, measure a signal composed of a sum of a zeroth order diffraction signal and a first order diffraction signal, repeat the measuring for a plurality of relations between the zeroth and the first diffraction signals, while maintaining the diffractive target and the illumination source stationary, and derive the first order diffraction signal from the measured sums. Illumination may be coherent and measurements may be in the pupil plane, or illumination may be incoherent and measurements may be in the field plane, in either case, partial overlapping of the zeroth and the first diffraction orders are measured. Illumination may be annular and the diffractive target may be a one cell SCOL target with periodic structures having different pitches to separate the overlap regions.

23 Claims, 6 Drawing Sheets

(51) Int. Cl.
    *G01B 9/02*     (2006.01)
    *G01N 21/47*     (2006.01)
    *G03F 7/20*     (2006.01)

(58) Field of Classification Search
    USPC .............................. 356/338, 342, 401, 508
    See application file for complete search history.

(56) References Cited

U.S. PATENT DOCUMENTS

| | | |
|---|---|---|
| 6,775,065 B2 | 8/2004 | Hayashi et al. |
| 7,403,293 B2 | 7/2008 | Pellemans et al. |
| 8,705,007 B2 | 4/2014 | Cramer et al. |
| 9,753,379 B2 * | 9/2017 | Singh .................... G01J 3/2823 |
| 9,910,366 B2 * | 3/2018 | Middlebrooks ..... G03F 7/70633 |
| 2006/0033921 A1 * | 2/2006 | Den Boef ........... G03F 7/70341 |
| | | 356/446 |
| 2007/0002336 A1 * | 1/2007 | Pellemans ........... G03F 7/70616 |
| | | 356/625 |
| 2011/0292365 A1 * | 12/2011 | Cramer .............. G01N 21/4785 |
| | | 355/67 |
| 2012/0033193 A1 * | 2/2012 | Van Der Schaar .......................... G01N 21/9501 |
| | | 355/67 |
| 2015/0176985 A1 * | 6/2015 | Shchegrov .............. H01L 22/12 |
| | | 356/614 |
| 2015/0204664 A1 * | 7/2015 | Bringoltz ............ G03F 7/70683 |
| | | 356/492 |

\* cited by examiner

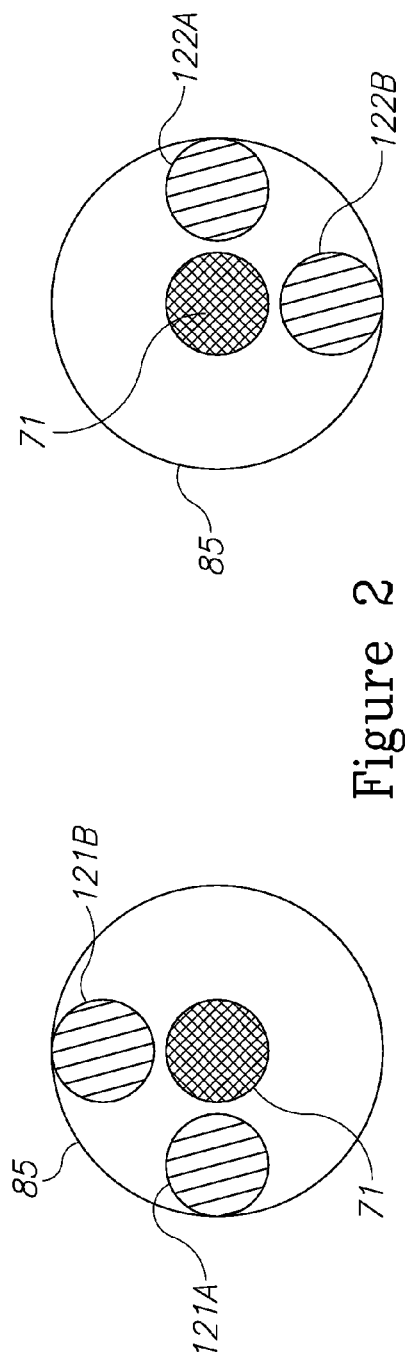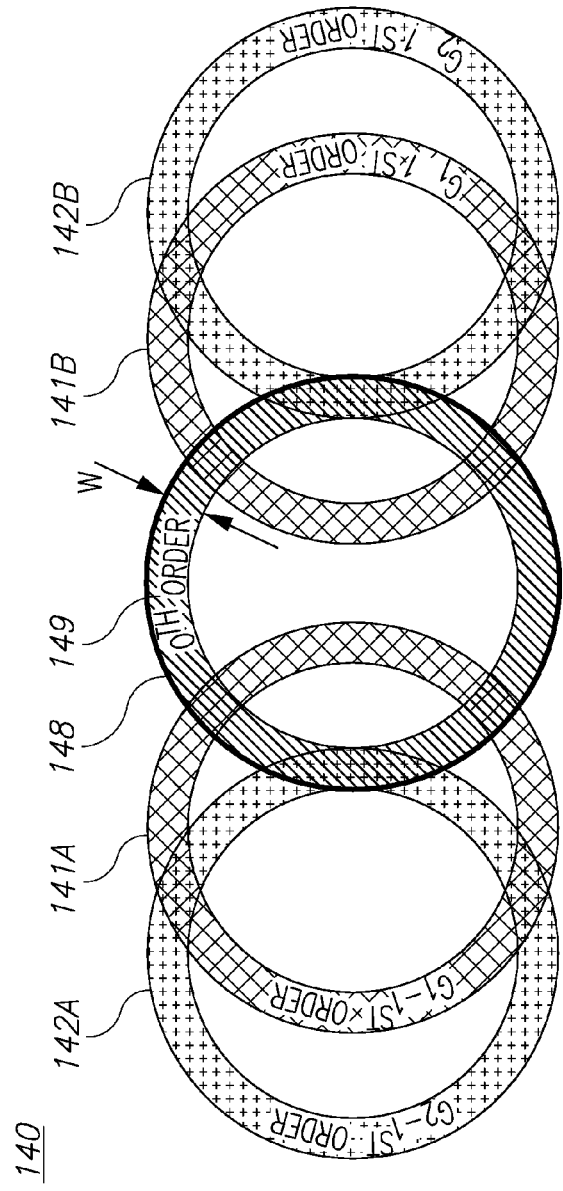

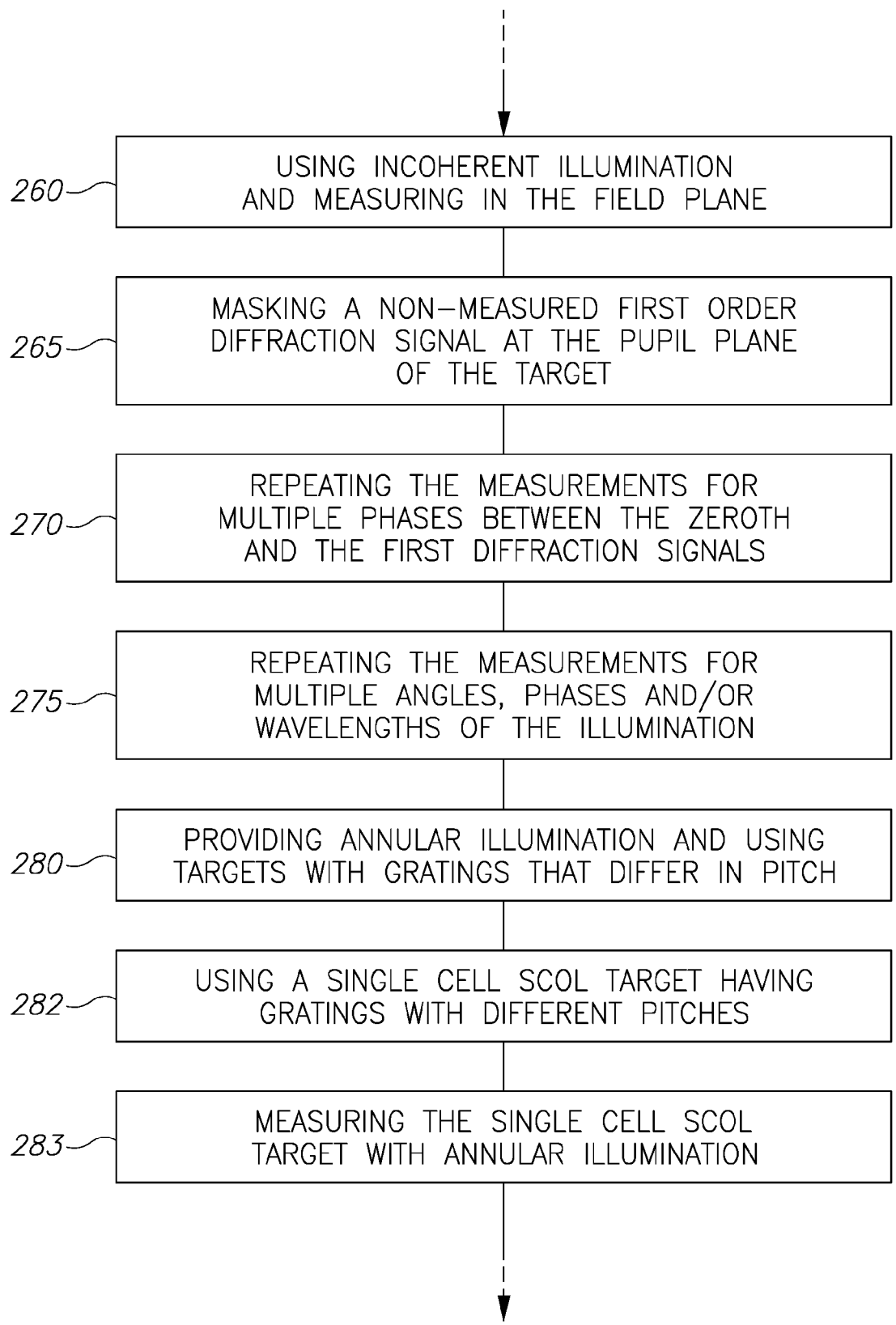
Figure 5 (cont. 1)

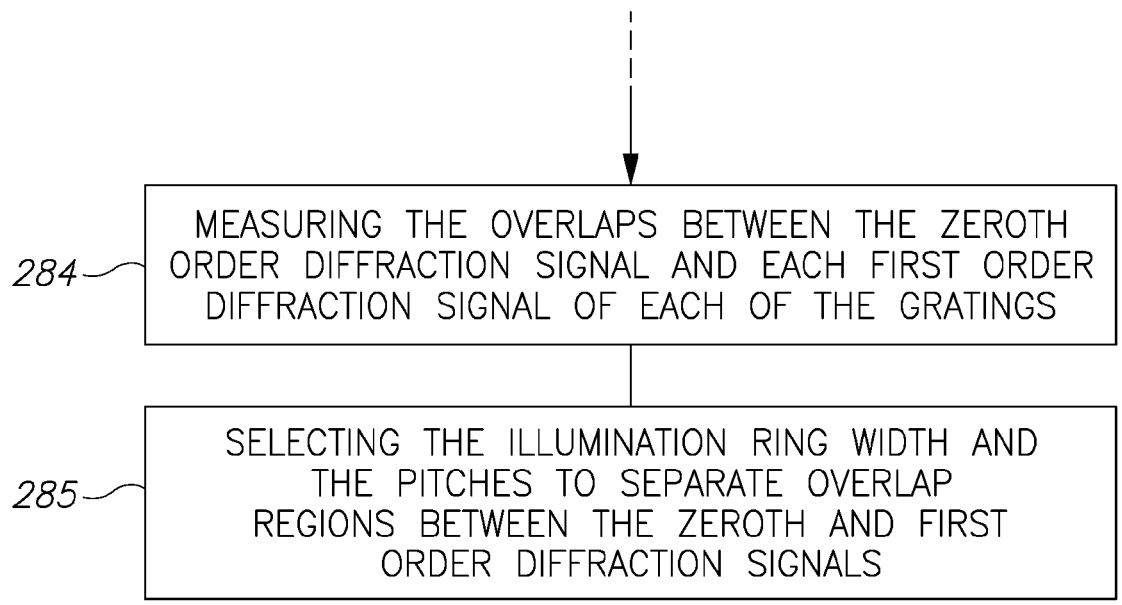
Figure 5 (cont. 2)

APPROACHES IN FIRST ORDER SCATTEROMETRY OVERLAY BASED ON INTRODUCTION OF AUXILIARY ELECTROMAGNETIC FIELDS

CROSS REFERENCE TO RELATED APPLICATIONS

This application claims the benefit of U.S. Provisional Patent Application No. 62/215,895 filed on Sep. 9, 2015, which is incorporated herein by reference in its entirety,

BACKGROUND OF THE INVENTION

1. Technical Field

The present invention relates to the field of scatterometry metrology, and more particularly, to measurements of single first order diffraction signals.

2. Discussion of Related Art

Angularly resolved scatterometry is being widely utilized for monitoring of overlay errors between stacked periodic structures (e.g., grating on grating targets).

U.S. Pat. No, 7,403,293, which is incorporated herein by reference in its entirety, discloses using a supercontinuum light source arranged to generate a measurement beam, an optical system arranged to direct the measurement beam onto the substrate and a sensor for detecting radiation reflected and/for diffracted by the structure.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides a metrology measurement method comprising: illuminating a stationary diffractive target by a stationary illumination source, measuring a signal composed of a sum of a zeroth order diffraction signal and a first order diffraction signal, repeating the measuring for a plurality of relations between the zeroth and the first order diffraction signals, while maintaining the diffractive target and the illumination source stationary, and deriving the first order diffraction signal from the measured sums.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 2 is a high level schematic illustration of pupil configurations (in the pupil plane) for measuring the signal in the field plane, according to some embodiments of the invention.

FIG. 3 is a high level schematic illustration of a pupil scheme with annular illumination diffracted from a target cell having periodic structure with different pitches, according to some embodiments of the invention.

DETAILED DESCRIPTION OF THE INVENTION

Figure 1:
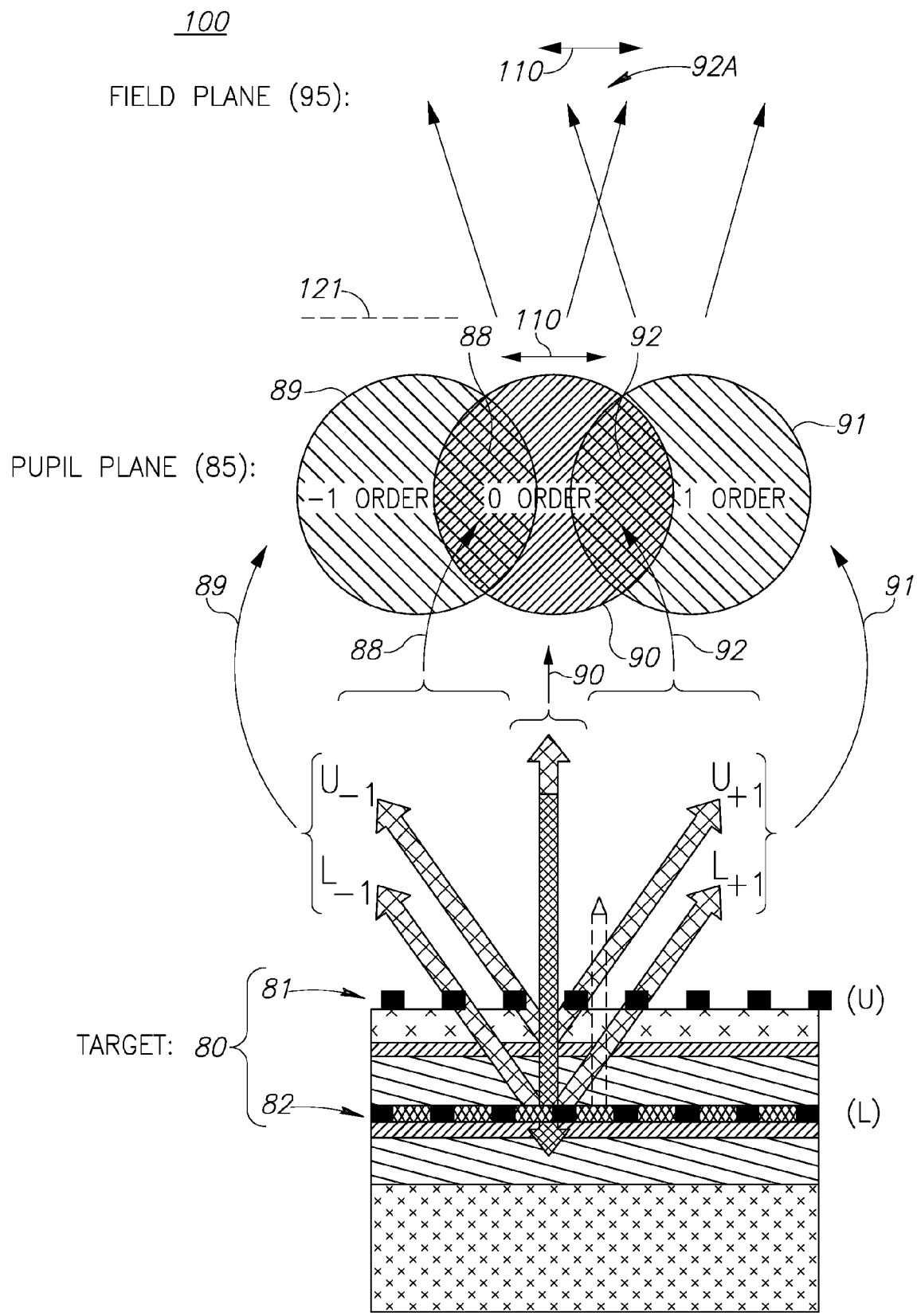
FIG. 1 is a high level schematic illustration of phase scanning in pupil or field planes respectively, by a metrology tool, according to some embodiments of the invention.

Prior to the detailed description being set forth, it may be helpful to set forth definitions of certain terms that will he used hereinafter.

The term "diffraction signal" as used in this application refers to the electromagnetic field which is diffracted off a periodic structure. The terms "zeroth order diffraction signal" and "first order diffraction signal" as used in this application refer to the electromagnetic field that is associated with the specified diffraction orders, namely the zeroth order and the first order. The +1 and −1 first order diffraction signals refer to the two lobes of the first order diffraction signal. The term "sum" as used in this application with respect to two diffraction order signals refers to the electromagnetic field resulting from the interference of the electromagnetic fields of the corresponding diffraction order signals.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways. Also, it is to he understood that the phraseology and terminology employed herein is for the purpose of description and should not be regarded as limiting.

Metrology measurement methods and tools are provided, which illuminate a stationary diffractive target by a stationary illumination source, measure a signal composed of a sum of a zeroth order diffraction signal and a first order diffraction signal, repeat the measuring for a plurality of relations between the zeroth and the first order diffraction signals, while maintaining the diffractive target and the illumination source stationary, and derive the first order diffraction signal from the measured sums. Illumination may be coherent and measurements may be in the pupil plane, or illumination may be incoherent and measurements may be in the field plane, in either case, partial overlapping of the zeroth and the first diffraction orders are measured. Illumination may be annular and the diffractive target may be a one cell SCOL (scatterometry overlay) target with periodic structures having different pitches to separate the overlap regions.

The present new approaches in first order scatterometry overlay are based on introduction of auxiliary electromagnetic fields to overcome a main disadvantage of standard scatterometry methods for overlay measurements, namely the lack of control over the topographic phase and the diffraction efficiency of the gratings, which cause indefinite enhancement of measurement errors such as resulting from target asymmetries and process instabilities.

For example, zeroth diffraction order signal, or any other interferometrically stabilized reference, may be used to enhance the SCOL signal on the detector. The amplitude of the SCOL signal may be retrieved by means of phase, scan of the zeroth order (or of the reference field) with respect to the first order signal, or by means of mapping the phase difference onto multi-pixel detector coordinate (camera).

In another example, different pitches of the individual gratings may be used to retrieve the phase of the diffracted electromagnetic field (i.e., diffracted illumination) by each one of the gratings. The phase may be derived from phase scan between illumination pupil points. Individual grating position may be derived from the phase difference of the corresponding diffraction orders and overlay may be retrieved from the difference of individual grating positions.

FIG. 1 is a high level schematic illustration of phase scanning 110 in pupil or field planes 85, 95 respectively, by a metrology tool 100, according to some embodiments of the invention. FIG. 1 depicts schematically a typical target cell in an overlay target 80 with periodic structures 81, 82 (e.g., gratings U and L, respectively), and the diffracted orders used in the measurement. Numeral 90 denoted zeroth order diffraction signal from target 80, numeral 91 denotes +1 first order diffraction signal from target 80 as sum of the diffracted signals from gratings 81, 82, $U_{+1}$, $L_{+1}$, respectively, and numeral 89 denotes −1 first order diffraction signal from target 80 as sum of the diffracted signals from gratings 81, 82, $U_{-1}$, $L_{-1}$, respectively. FIG. 1 further illustrates regions 88, 92 in pupil plane 85 in which zeroth order diffraction signal 90 overlaps −1 and +1 first order diffraction signals 89, 91 respectively, with phase scanning illustrated schematically by the arrow. In field plane 9 an exemplary sum of zeroth order diffraction signal 90 and +1 first order diffraction signal 91 is shown schematically as region 92A (with −1 first order diffraction signal 89 blocked by mask 121, see FIG. 2), which may be modified by phase scanning 110 (see further explanation below).

The signal in first order scatterometry configuration is a result of interference between first diffraction orders of the upper and bottom gratings 81, 82 respectively, having the same pitch. The diffracted electromagnetic field from either upper (U) or lower (L) periodic structures 81, 82, respectively, can be expressed as $$E_{U,L}^{(\pm 1)} = A_{U,L}^{(\pm 1)} e^{i[\pm \frac{2\pi}{P}(OVL+f_0)+\Psi_{U,L}]},$$

with ±1 denoting the respective first order diffraction order, $A_u$ and $A_L$ denote the amplitudes of the diffraction orders of individual gratings (related to their diffraction efficiency), phases $\Psi_u$ and $\Psi_L$ correspond to the topographic phases stemming in stack parameters mutual to the positive and negative diffraction orders, and $\pm f_0$ denote designed shifts (offsets) between gratings 81, 82 (having a pitch P) in respective target cells. The intensity of the diffraction orders, $I^{\pm 1}(\pm f_0)$, depends on the diffractive efficiencies of gratings 81, 82 and on the topographic phase difference $\Psi_u - \Psi_L$, as expressed in Equation 1:

$$I^{\pm 1}(\pm f_0) = |E_{SCOL}^{(\pm 1)}|^2 = |E_U^{(\pm 1)} + E_L^{(\pm 1)}|^2 = \quad \text{Equation 1}$$

$$A_U^2 + A_L^2 + 2A_U A_L \cos\left[\Psi_U - \Psi_L \pm \frac{2\pi}{P}(OVL \pm f_0)\right] =$$

$$|A_{SCOL}^{(\pm 1)} E^{i\Psi_{SCOL}}|^2 = |A_{SCOL}^{(\pm 1)}|^2$$

The differential signal (D) for each angle of illumination (pupil point) is given as intensity difference between +1 and −1 first diffraction orders, expressed in Equation 2:

$$D(\pm f_0) = \quad \text{Equation 2}$$

$$I^1(\pm f_0) - I^{-1}(\pm f_0) \approx A_U A_L \sin(\Psi_U - \Psi_L) \sin\left[\frac{2\pi}{P}(OVL \pm f_0)\right]$$

Measurements of the differential signal D, measured at the $\pm f_0$ cells provides the overlay (OVL).

Despite the conceptual simplicity of the method, there are several fundamental problems regarding the above expressions, for example: (i) Whenever the diffraction efficiency of the gratings ($A_U$ and $A_L$) is small, the signal. intensity (expressed in Equation 1) is small and can be lower than the detector noise level (limited light budget). (ii) Whenever the diffraction efficiency of either of the gratings ($A_U$ or $A_L$) is small, the differential signal might be undetectable within optical noise levels of the measurement system (expressed in Equation 2), or within the scattering of the non-periodic target defects (i.e., within target noise). (iii) For targets with high topography it happens that the effective optical path difference of the electromagnetic fields diffracted by top and bottom gratings is an integer multiple of $$\frac{\lambda}{2},$$

where λ is the wavelength of illumination. In such a situation, the differential signal vanishes irrespective of the overlay (($\Psi_U - \Psi_L$)=mπ, with integer m), indicating lack of sensitivity to overlay (Equation 2). In order to overcome the latter problem thee differential signal must be measured over a broad range of topographical phases and select values that provide sufficient sensitivity to the overlay and/or to increase the covered range of angles of incidence, which for a standard SCOL configuration is strongly limited by required separation of the first diffraction orders from the zeroth diffraction order. The disclosed new approaches for overlay scatterometry overcome these typical problems of the standard first order scatterometry configuration, and further enable use of an increased range of angles of incidence and/or topographic phases.

High sensitivity to overlay is often achieved in condition of low signal, meaning that measurement capabilities are often compromised. In a standard first order scatterometry configuration a small illumination NA (numerical aperture) is used in order to separate the pupil areas corresponding to 0 and first diffraction orders. Instead, the present invention implements overlay scatterometry that utilizes the full illumination e.g., up to NA~0.9. As illustrated in FIG. 1, in areas in the pupil corresponding to overlapping of zeroth and first diffraction orders, the electromagnetic field is expressed in Equation 3:

$$E(\vec{\theta}) = E^{(0)}(-\vec{\theta}) + E_U^{(\pm 1)}\left(-\vec{\theta} \mp \frac{\lambda}{P}\hat{e}_x\right) + E_L^{(\pm 1)}\left(-\vec{\theta} \mp \frac{\lambda}{P}\hat{e}_x\right) =$$
$$E^{(0)}(-\vec{\theta})e^{i\Phi(-\vec{\theta})} + \left[E_U^{(\pm 1)}\left(-\vec{\theta} \mp \frac{\lambda}{P}\hat{e}_x\right) + E_L^{(\pm 1)}\left(-\vec{\theta} \mp \frac{\lambda}{P}\hat{e}_x\right)\right]e^{i\Phi\left(-\vec{\theta}\mp\frac{\lambda}{P}\hat{e}_x\right)}$$

Equation 3 with $\vec{\theta}$ denoting the collection pupil coordinate, $\lambda$ and P are the illumination wavelength and grating pitches, respectively, $\hat{e}_x$ is a unit vector in the grating direction and $\Phi(\vec{\theta})$ is a phase function as control parameter.

The intensity measured at every point of the collection pupil is expressed in Equation 4:

$$I(\vec{\theta}) = \left|E^{(0)}(-\vec{\theta})\right|^2 + \left|E_U^{(\pm 1)}\left(-\vec{\theta} \mp \frac{\lambda}{P}\hat{e}_x\right) + E_L^{(\pm 1)}\left(-\vec{\theta} \mp \frac{\lambda}{P}\hat{e}_x\right)\right|^2 +$$
$$2E^{(0)}(-\vec{\theta})\left[E_U^{(\pm 1)}\left(-\vec{\theta} \mp \frac{\lambda}{P}\hat{e}_x\right) + E_L^{(\pm 1)}\left(-\vec{\theta} \mp \frac{\lambda}{P}\hat{e}_x\right)\right]\cos\left[\Phi(-\vec{\theta}) - \Phi\left(-\vec{\theta} \mp \frac{\lambda}{P}\hat{e}_x\right)\right] =$$
$$I_0(-\vec{\theta}) + I^{(\pm 1)}\left(-\vec{\theta} \mp \frac{\lambda}{P}\hat{e}_x\right) +$$
$$2\sqrt{I_0(-\vec{\theta})I^{(\pm 1)}\left(-\vec{\theta} \mp \frac{\lambda}{P}\hat{e}_x\right)}\cos\left[\Phi(-\vec{\theta}) - \Phi\left(-\vec{\theta} \mp \frac{\lambda}{P}\hat{e}_x\right) - \Psi_{SCOL}\left(-\vec{\theta} \mp \frac{\lambda}{P}\hat{e}_x\right)\right]$$

Equation 4 the term $$\Psi_{SCOL}\left(-\vec{\theta} \mp \frac{\lambda}{P}\hat{e}_x\right)]$$

from Equation 4 representing the modulation of intensity in every point of the collection pupil as the phase between illumination points is varied. The amplitude of the modulation measured over a sufficient range of applied phase figures in the illumination path may be used to calculate the intensity of the diffraction orders, which later may be used to calculate the overlay between the upper and lower gratings. In this way, a much larger area of the collection pupil can be utilized for signal detection, allowing probing a broader range of topographic phases.

An alternative formulation of Equation 4 is presented in Equation 5:

$$I = A_0^2 + A_1^2 + A_2^2 + 2A_1A_2\cos\left[\Psi_1 - \Psi_2 \pm \frac{2\pi}{P}(OVL \pm f_0)\right] +$$
$$2A_0A_1\cos\left[\Psi_0 - \Psi_1 \mp \frac{2\pi}{P}(x - GP_1)\right] +$$
$$2A_0A_2\cos\left[\Psi_0 - \Psi_2 \mp \frac{2\pi}{P}(x - GP_2)\right],$$

Equation 5 in which $A_0$ and $\Psi_0$ are the amplitude and the phase, respectively, of the zeroth diffraction order, $GP_1$ and $GP_2$ are the grating positions ($OVL \pm f_0 = GP_1 - GP_2$) and x is the scanning parameter that corresponds to the position of the illumination spot center. The two last terms may be converted into the following form, expressed in Equation 6:

$$2A_0A_1\cos\left[\Psi_0 - \Psi_1 \mp \frac{2\pi}{P}(x - GP_1)\right] +$$
$$2A_0A_2\cos\left[\Psi_0 - \Psi_2 \mp \frac{2\pi}{P}(x - GP_2)\right] =$$
$$2A_0\sqrt{A_1^2 + A_2^2 + 2A_1A_2\cos\left[\Psi_1 - \Psi_2 \pm \frac{2\pi}{P}(OVL \pm f_0)\right]} \cdot$$
$$\cos\left[\Psi_0 - \frac{\Psi_1 + \Psi_2}{2} - \frac{\pi}{P}x + \frac{\pi}{P}(GP_1 + GP_2) + \tan^{-1}\frac{(A_1 - A_2)\tan\left(\frac{\Psi_1 - \Psi_2}{2} \pm \frac{2\pi}{P}(OVL \pm f_0)\right)}{A_1 + A_2}\right]$$

Equation 6

Scanning the illumination spot in the grating direction, i.e., changing the parameter x in Equation 6, e.g., by using a scanning minor in the pupil, and performing a fit to the amplitude of the measured signal, is equivalent to measuring the following signal, expressed in Equations 7:

$$I_m = 2A_0\sqrt{A_1^2 + A_2^2 + 2A_1A_2\cos\left[\Psi_1 - \Psi_2 \pm \frac{2\pi}{P}(OVL \pm f_0)\right]}$$

Equations 7 and, correspondingly, $$I_m^2 = 4A_0^2\left(A_1^2 + A_2^2 + 2A_1A_2\cos\left[\Psi_1 - \Psi_2 \pm \frac{2\pi}{P}(OVL \pm f_0)\right]\right),$$

the latter being the signal measured in the standard scatterometry configuration, multiplied by the square of the zero diffraction order amplitude. In the words using the described procedure the standard SCOL signal is retrieved, and is detected as a controlled modulation of a much higher signal of the zeroth diffraction order, which may be up to a hundred times stronger in a case of low diffraction efficiency.

System 100 and method 200 may employ any of the following ways to scan the phase between the illumination points, such as (i) using an adaptive phase element (e.g., a DLP—Digital Light Processing element) in the illumination path of the scatterometer to introduce and use any phase pattern; (ii) using a mirror with an adjustable tilt angle, positioned within the illumination pupil to provide a linear phase scan between points using the tilt angle; and (iii) modifying the axial position of the target with respect to the illumination/collection lens using defocus aberration to introduce the phase variation.

Alternatively or complementarily, the signal may be measured in the field plane (95) while selecting proper diffraction orders in the collection pupil (85). FIG. 2 is a high level schematic illustration of pupil configurations (in pupil plane 85) for measuring the signal in field plane 95, according to some embodiments of the invention. For example, interchangeable mask(s) 121, 122 may be used in collection pupil 85, allowing transmission of zeroth and alternatingly ±1 first diffraction orders. In such a setup, the enhanced SCOL signal appears as the amplitudes of the pitch harmonics in the image, and may be retrieved by standard image processing methods. Alternatively, the combinations of zeroth order with ±1 first diffraction orders may be detected simultaneously on different detectors, by using specially designed optics for separation of the orders (see FIG. 4A). Such field plane detection has the advantage of simultaneous measurement of all the target cells. For example, FIG. 2 schematically illustrates central illumination 71 and, to the left, blocking the −1 diffraction orders (89) by mask elements 121A, 121B (i.e., in x and y directions) and measuring the sum of zeroth and +1 order 90 and 91 respectively; and to the right, blocking the +1 diffraction orders (91) by mask elements 122A, 122B (i.e., in x and y directions) and measuring the sum of zeroth and −1 order 90 and 89 respectively. This configuration allows measurement of both cells with different offsets $\pm f_0$ and X,Y targets simultaneously. Separation of zeroth and first diffraction orders in the pupil allows additional control over the amplitude of the reflected zero order. The measured signal is as expressed in Equation 5A:

$$I = A_0^2 + A_U^2 + A_L^2 + 2A_U A_L \cos\left[\Psi_U - \Psi_L \pm \frac{2\pi}{P}(OVL \pm f_0)\right] + \quad \text{Equation 5A}$$

$$2A_0 A_U \cos\left[\Psi_0 - \Psi_U \mp \frac{2\pi}{P}(x - GP_U)\right] +$$

$$2A_0 A_L \cos\left[\Psi_0 - \Psi_L \mp \frac{2\pi}{P}(x - GP_L)\right],$$

with x being a field parameter, e.g., a coordinate at the detector, avoiding the requirement to scan the phase. Fitting the amplitude of the periodic signal in the field, the signal becomes $I_m$ that is expressed in Equation 7A:

$$I_m = \quad \text{Equation 7A}$$
$$2A_0 \sqrt{A_U^2 + A_L^2 + 2A_U A_L \cos\left[\Psi_U - \Psi_L \pm \frac{2\pi}{P}(OVL \pm f_0)\right]}$$

In case of using multiple detectors, two or more images may be grabbed simultaneously, at least one image comprising the zeroth and the +1 first diffraction orders and at least another image comprising the zeroth and the −1 first diffraction orders. For example an optical element (e.g., orders separating optics 124 of FIG. 4A) may positioned in the vicinity of collection, pupil 85 of the optical system to redirect each half of the pupil toward different detectors 126. The positioning errors of the optical element may be compensated for by normalizing the image by the square root of the total intensity of corresponding part of the zeroth order. Alternatively, for targets with low diffraction efficiency, normalization may be achieved algorithmically, by normalizing the image with respect to the square root of its average grey level. This configuration allows for significant boost in MAM (move-acquire-measure) time.

Yet another option for field plane measurement may be realized by alternating off-axis illumination. If illumination center is sufficiently displaced from normal illumination, e.g., by beam displacer 108 illustrated schematically in FIG. 4A, only the zeroth and either the +1 first or −1 first diffraction orders reaches the collection pupil at any time. Performing sequential measurements with two symmetric off-axis illumination points enables to capture images necessary for overlay measurements with no need for additional phase scan. Additionally and advantageously, if angles of incidence and the wavelengths to pitch ratio are chosen to be close to Littrow configuration (identical diffraction incidence angles), the dependency of the signal on defocusing; may be significantly suppressed.

In certain embodiments, the target may be an imaging target (e.g., AIM—advanced imaging metrology target) comprising two or more periodic structures (with a same pitch or with different pitches). The metrology tool may be further configured to carry out at least two overlay measurements of the target (in the field plane), at least one, with a blocked +1 diffraction order and at least another one with a blocked −1 diffraction order, and derive an overlay (i.e., the displacement between the periodic structures) by averaging the at least two overlay measurements. The measurement may comprise one or multiple alterations between blocking +1 and −1 diffraction orders.

FIG. 3 is a high level schematic illustration of a pupil scheme 140 with annular diffracted from a target cell having periodic structure with different pitches, according to some embodiments of the invention. Using diffractive targets with different pitches for the at least two periodic structures, in a non-limiting example, top and bottom gratings 151, 152 (see e.g., FIG. 4B, denoted $G_1$ and $G_2$, respectively, in FIG. 3) allows to separate spots in the pupil corresponding to the diffraction of top and bottom gratings. Organizing the illumination scheme in a way that allows overlap between zeroth order and first diffraction orders of each one of different gratings 151, 152 at least partially separately, to enhance the signal of each one of the gratings and determine the position of each one of the gratings separately. Without loss of generality, FIG. 3 exemplifies a possible pupil scheme 140 allowing for such a measurement. Pupil scheme 140 comprises zeroth order diffraction signal 149, having a width W that represents a ring width of the annular illumination, −1 first diffraction signals 141B, 142B of periodic structures 151, 152, respectively as distinct rings, and −1 first diffraction signals 141A, 142A of periodic structures 151, 152, respectively as distinct rings, in a non-limiting example of lower grating 152 having a smaller pitch than upper grating 151 ($P_2 < P_1$). A black circle around zeroth order signal 149 denoted a possible collection NA 148, which includes separate regions for signal 149, signals 141A, B, and overlaps (sums) of signal 149 with all four signals 141A, 141B, 142A, 142B. Collection NA 148 may be select to have different sizes that may be determined by metrology requirements.

The (summed) signal at pupil points with overlapping first diffraction order signals 141A, B of first grating 151 overlaps with zeroth diffraction order 149 may be expressed as in Equations 8:

$$I_1^1 = \left(A_0 e^{i\Psi_0} + A_1 e^{2\pi i\left[\frac{(GP_1-X)}{P_1} + \frac{\Psi_1}{2\pi}\right]}\right)^2 = \quad \text{Equations 8}$$

$$A_0^2 + A_1^2 + 2A_0 A_1 \cos\left[\frac{2\pi}{P_1}(GP_1 - X) + (\Psi_1 - \Psi_0)\right]$$

$$I_{-1}^1 = \left(A_0 e^{i\Psi_0} + A_{-1} e^{-2\pi i\left[\frac{(GP_1-X)}{P_1} - \frac{\Psi_1}{2\pi}\right]}\right)^2 =$$

$$A_0^2 + A_{-1}^2 + 2A_0 A_{-1} \cos\left[\frac{2\pi}{P_1}(GP_1 - X) - (\Psi_1 - \Psi_0)\right]$$

with $I_1^1$ and $I_{-1}^1$ representing the intensities in the pupil regions of the overlap of $0^{th}$ order with $1^{st}$ and $-1^{st}$ diffraction orders of grating 151 (indicated by superscript 1); $P_1$ is the pitch of first grating 151; $A_0$, $A_1$ and $A_{-1}$ denote the amplitudes of the $0^{th}$, $1^{st}$, and $-1^{st}$ diffraction orders respectively, $GP_1$ denotes the position of first grating 151, and X denotes the position of the illumination spot with respect to grating 151, and $\Psi_1$ and $\Psi_0$ are topographic phases of the first and zeroth diffraction order signals of the grating under consideration. Similarly, the signals for grating 152 may be calculated. Scanning, e.g., using optical means, the position of the illumination spot with respect to the grating, or, alternatively scanning the phase of the illumination ($\Psi_0$) by means of controllable aberration in illumination, one can retrieve the position of each one of the gratings. The difference between the resulting two grating positions is the overlay. It is noted that the lack of requirement for interference signal between diffraction orders of the two gratings allows to perform the measurements while optimizing the signal separately for each one of the layers, e.g. by means of different wavelength, polarization integration time etc.

Phase scan between interferometrically stable electromagnetic fields may thus be utilized to retrieve the amplitude of the SCOL signal in the area of spatial overlap of the fields. Different pitches of the individual gratings may be utilized to allow retrieval of the phase of the diffracted electromagnetic field by each one of the gratings. The phase may be derived from phase scan between illumination pupil points, or, in certain embodiments, by means of target displacement with respect to optical axis or by means of optical axis displacement with respect to the target. The individual grating positions may be derived from the phase difference between the corresponding diffraction orders, and the overlay may be retrieved from the difference of individual grating positions.

Figure 4A:
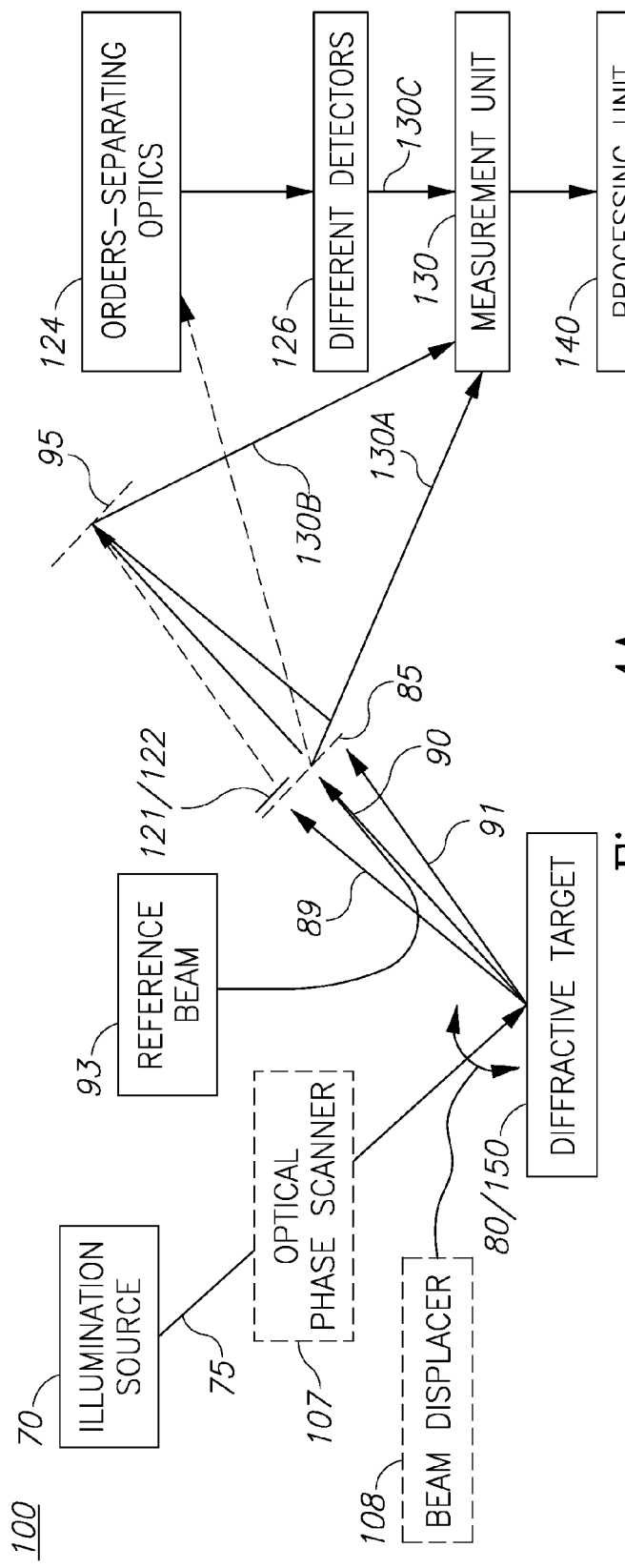
FIG. 4A is a high level schematic block diagram of the metrology tool according to some embodiments of the invention.

FIG. 4A is a high level schematic block diagram of metrology tool 100, according to some embodiments of the invention. FIG. 4A illustrates multiple, measurement arrangements, which may be used alternatively or complementarily. Metrology tool 100 comprises a stationary illumination source 70 configured to illuminate stationary diffractive target 80 or 150, a measurement unit 130 configured to measure, repeatedly, a signal composed of a sum of zeroth order diffraction signal 90 and a first order diffraction signal 91 or 89 (the former is illustrated in a non-limiting manner), wherein the repeated measuring is carried out for a plurality of relations between zeroth and first diffraction signals 90, 91 respectively, while maintaining diffractive target 80 or 150 and illumination source 70 stationary, and a processing unit 140 configured to derive first order diffraction signal 91 from the measured sums. Measurement Unit 130 may be configured to carry out the measurements in pupil plane 85 (marked 130A) and/or in field plane 95 (marked 130B), as explained above.

The illuminating may be coherent and the measuring may be carried out in pupil plane 85 (illustrated schematically) with respect to target 80 or 150. The illumination wavelength and the pitch of target 80 or 150 may he selected to yield partial overlapping of zeroth and first diffraction orders 90, 91 respectively in pupil plane 85.

The illuminating may be incoherent and the measuring may be carried out in field plane 95 (illustrated schematically) with respect to target 80 or 150. Metrology tool 100 may further comprise a mask 121 or 122 at pupil plane 85 of target 80 or 150, mask 121 or 122 being configured to block a non-measured first order diffraction signal (in the non-limiting illustrated case −1 diffraction order 89) to yield the measured sum.

Metrology tool 100 may be configured to identify, during a training stage, and then remove inaccuracy-introducing illumination points. Using and optimizing the illumination pattern in the training stage may enable to avoid contribution of illumination points that introduce inaccuracy to the measurements. Inaccuracy-introducing illumination points may be found during train (e.g., during recipe selection), by observing the field image while scanning over the illumination points, or by analyzing the pupil image received from the target. The latter option may additionally involve introduction of special, one cell "train" targets, or may involve reducing the field of view down to a single cell, in order to enable accurate pupil analysis. Inaccuracy-introducing illumination points may he identified as points having low sensitivity to the overlay between the gratings, or using inverse contrast of the final image. The identified inaccuracy-introducing illumination points may be removed, i.e., excluded from illumination scheme, in the actual measurement (after the training phase) e,g., using a controlled pixelated illuminator.

Measurement unit 130 may be further configured to carry out the repeated measuring for a plurality of phases as the relations between zeroth and first diffraction signals 90, 91 respectively. Measurement unit 130 may be further configured to carry out the repeated measuring for a plurality of angles and/or phases and/or wavelengths of the illumination to modify the relations between zeroth and first diffraction signals 90, 91 respectively. Metrology tool 100 may further comprise an optical phase scanner 107 (e.g., a digital light processing element DLP, a tiltable mirror, a focus aberrating element etc.) configured to carry out the repeated phase measurements (phase scanning 110, as in FIG. 1). A reference beam 93 (shown schematically in FIG. 4A) may be used in place of or in addition to zeroth order diffraction signal 90 to enhance the measurement capabilities of the first diffraction signals as described herein. Metrology tool 100 may further comprise a beam displacer 108 configured to modify an illumination beam incidence angle between the repeated measurements. It is noted that phase scanning may be replaced or enhanced by physically moving target 80 or 150, illumination source 70 and/or the measurement plane.

Metrology tool 100 may further comprise an orders-separating optics 124 configured to separate field signals relating to different diffraction orders to be measured by respective at least two detectors 126, associated with measurement unit 130, for measuring the separated field signals (indicated as 130C, clearly detectors 126 may be part of measurement unit 130). The combinations of zeroth order with ±1 first diffraction orders may be detected simultaneously on different detectors, by using specially designed optics for separation of the orders. Such field plane detection has the advantage of simultaneous measurement of all the target cells.

Figure 4B:
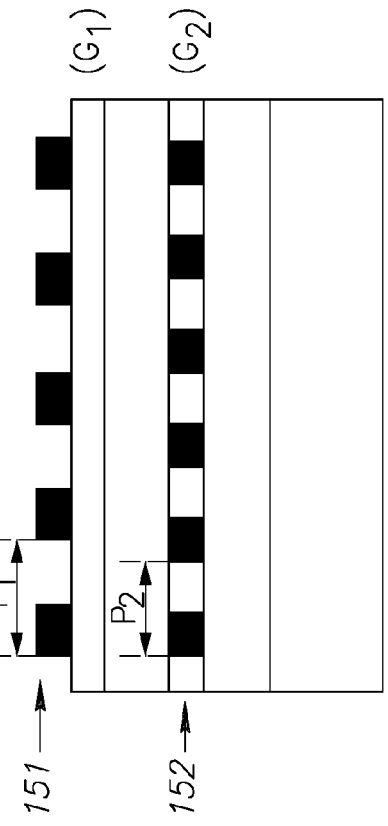
FIG. 4B is a high level schematic illustration of a diffractive target, according to some embodiments of the invention.

FIG 4B is a high level schematic illustration of diffractive target 150, according to some embodiments of the invention. The illumination may be annular and diffractive target 150 may comprise at least two periodic structures 151, 152 having at least two corresponding different pitches P1, P2 respectively. A width of the annular illumination (W, see FIG. 3) and pitches P1 and P2 may be selected to separate overlap regions between zeroth order diffraction signal 90 and each of first order diffraction signals 89, 91 from each of periodic structures 151, 152. Certain embodiments comprise diffractive target 150 as a single cell SCOL target, with the metrology tool and measurements are configured to determine phase information from the signal diffracted off the single cell SCOL target, as explained above.

Figure 5:
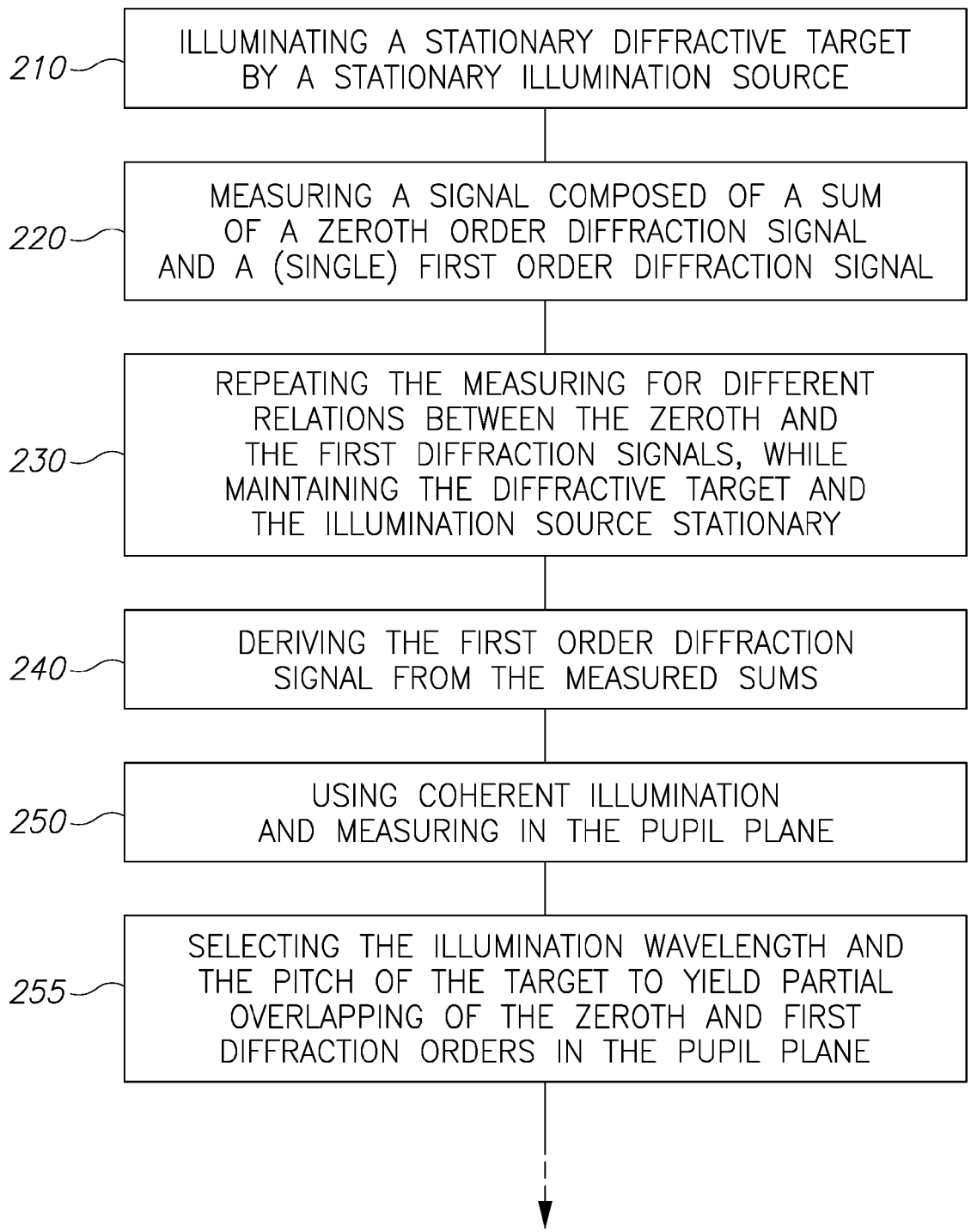
FIG. 5 is a high level flowchart illustrating a metrology measurement method, according to some embodiments of the invention.

FIG. 5 is a high level flowchart illustrating a metrology measurement method 200, according to some embodiments of the invention. Method 200 may be at least partially implemented by at least one computer processor, e.g., in a metrology module. Certain embodiments comprise computer program products comprising a computer readable storage medium having computer readable program embodied therewith and configured to carry out of the relevant stages of method 200. Certain embodiments comprise target design files of respective targets designed by embodiments of method 200. Certain embodiments comprise metrology signals derived by method 200 and/or by tool 100.

Metrology measurement method 200 comprises illuminating a stationary diffractive target by a stationary illumination source (stage 210), measuring a signal composed of a sum of a zeroth order diffraction signal and a first order diffraction signal (stage 220), repeating the measuring for a plurality of relations between the zeroth and the first order diffraction signals, while maintaining the diffractive target and the illumination source stationary (stage 230), and deriving the first order diffraction signal from the measured sums (stage 240).

Method 200 may comprise providing coherent illuminating and measuring in the pupil plane (stage 250) so that illuminating 210 is carried out with coherent illumination and measuring 220, 230 are carried out in a pupil plane with respect to the target. Method 200 may further comprise selecting the illumination wavelength and the pitch of the target to yield partial overlapping of the zeroth and first diffraction orders in the pupil plane (stage 255).

Method 200 may comprise providing incoherent illuminating and measuring in the field plane (stage 260) so that illuminating 210 is carried out with incoherent illumination and measuring 220, 230 are carried out in a field plane with respect to the target. Method 200 may further comprise masking a non-measured first order diffraction signal at the pupil plane of the target (stage 265) to yield the measured sum. Method 200 may further comprise carrying out at least two overlay measurements of an imaging target (comprising at least two periodic structures such as gratings, with same or different pitches, e.g., AIM targets), at least one of the measurements with a masked +1 diffraction order and at least another one of the measurements with a masked −1 diffraction order, and deriving an overlay by averaging the at least two overlay measurements. Method 200 may further comprise identifying, during a training stage, and removing inaccuracy-introducing illumination points, as explained above.

Method 200 may comprise carrying out the repeated measuring for a plurality of phases as the relations between the zeroth and the first order diffraction signals (stage 270), and/or by carrying out the repeated measuring for a plurality of angles and/or phases and/or wavelengths of the illumination to modify the relations between the zeroth and the first order diffraction signals (stage 275).

Method 200 may comprise providing annular illumination and using targets with gratings that differ in pitch (stage 280), so that the illumination is annular and the diffractive target comprises at least two periodic structures having at least two corresponding different pitches. Method 200 may further comprise selecting the illumination width and the pitches to separate overlap regions between the zeroth and first order diffraction signals (stage 285), e.g., to separate overlap regions between the zeroth order diffraction signal and each of the first order diffraction signals from each of the respective periodic structures.

Method 200 may comprise using a single cell SCOL target having gratings with different pitches (stage 282), measuring the single cell SCOL target with annular illumination (stage 283) and measuring the overlaps between the zero order diffraction signal and each first order diffraction signal of each of the gratings (stage 284).

Advantageously, disclosed systems 100 and methods 200 provide new optical configuration which achieve a superior accuracy in scatterometry overlay measurement, improves tool performance and reduces effect of process variations. Moreover, disclosed systems 100 and methods 200 allow detecting more than a single diffraction order at the detector position in gratine-over-gratine target, retrieve information by phase scan between illumination points, and organize phase scan between first diffraction orders and either zeroth diffraction order or a reference beam by either target displacement or illumination spot displacement. Scanning phase between diffraction orders may be carried out by introducing controllable aberrations in illumination, i.e. by adaptive optical elements. Systems 100 and methods 200 enable measurement of the modulation amplitude of the grating-over-grating target in the field plane while more than a single diffraction order is allowed at the detector. Systems 109 and methods 200 also enable measurement of grating-over-grating targets with different pitches and retrieval of grating positions (and overlay) by modulation of the phases of the diffraction orders and capturing respective pupil images. Finally, disclosed systems 100 and methods 200 improve the accuracy of overlay measurements and extend the applicability of scatterometry to previously hardly addressable layers.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be, implemented in a single embodiment.

Certain embodiments of the invention may include features from different embodiments disclosed above, and certain embodiments may incorporate elements from other embodiments disclosed above. The disclosure of elements of the invention in the context of a specific, embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding, descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology measurement method comprising:
illuminating a stationary diffractive target by a stationary illumination source,
measuring a scatterometry signal composed of a sum of a zeroth order diffraction signal and a first order diffraction signal with a detector,
repeating the measuring for a plurality of relations between the zeroth and the first order diffraction signals, while maintaining the diffractive target and the illumination source stationary, and
deriving the first order diffraction signal, using a processor, from the measured sums.

2. The metrology measurement method of claim 1, wherein the illuminating is coherent and the measuring is carried out in a pupil plane with respect to the target.

3. The metrology measurement method of claim 2, wherein an illumination wavelength and a pitch of the target are selected to yield partial overlapping of the zeroth and the first diffraction orders in the pupil plane.

4. The metrology measurement method of claim 1, wherein the illuminating is incoherent and the measuring is carried out in a field plane with respect to the target.

5. The metrology measurement method of claim 4, wherein a non-measured first order diffraction signal is masked at the pupil plane of the target to yield the measured sum.

6. The metrology measurement method of claim 5, wherein the target is an imaging target comprising at least two periodic structures, the method further comprising carrying out at least two overlay measurements of the target, at least one with a masked +1 diffraction order and at least another one with a masked −1 diffraction order, and deriving an overlay by averaging the at least two overlay measurements.

7. The metrology measurement method of claim 4, further comprising identifying, during a training stage, and removing inaccuracy-introducing illumination points.

8. The metrology measurement method of claim 2, further comprising carrying out the repeated measuring for a plurality of phases as the relations between the zeroth and the first order diffraction signals.

9. The metrology measurement method of claim 2, further comprising carrying out the repeated measuring for a plurality of angles and/or phases and/or wavelengths of the illumination to modify the relations between the zeroth and the first order diffraction signals.

10. The metrology measurement method of claim 1, wherein the illumination is annular and the diffractive target comprises at least two periodic structures having at least two corresponding different pitches, and wherein a width of the annular illumination and the pitches are selected to separate overlap regions between the zeroth order diffraction signal and each of the first order diffraction signals from each of the respective periodic structures.

11. A metrology tool comprising:
a stationary illumination source configured to illuminate a stationary diffractive target,
a measurement unit that includes at least one detector, wherein the measurement unit is configured to measure, repeatedly, a scatterometry signal composed of a sum of a zeroth order diffraction signal and a first order diffraction signal, wherein the repeated measuring is carried out for a plurality of relations between the zeroth and the first order diffraction signals, while maintaining the diffractive target and the illumination source stationary, and
a processor configured to derive the first order diffraction signal from the measured sums.

12. The metrology tool of claim 11, wherein the illuminating is coherent and the measuring is carried out in a pupil plane with respect to the target.

13. The metrology tool of claim 12, wherein an illumination wavelength and a pitch of the target are selected to yield partial overlapping of the zeroth and the first order diffraction orders in the pupil plane.

14. The metrology tool of claim 11, wherein the illuminating is incoherent and the measuring is carried out in a field plane with respect to the target.

15. The metrology tool of claim 14, further comprising a mask at the pupil plane of the target, the mask configured to block a non-measured first order diffraction signal to yield the measured sum.

16. The metrology tool of claim 15, wherein the target is an imaging target comprising at least two periodic structures, and the metrology tool is further configured to carry out at least two overlay measurements of the target, at least one with a blocked +1 diffraction order and at least another one with a blocked −1 diffraction order, and derive an overlay by averaging the at least two overlay measurements.

17. The metrology tool of claim 14, further comprising an orders-separating optics configured to separate field signals relating to different diffraction orders, wherein the measurement unit comprises at least two of the detectors for measuring the separated field signals.

18. The metrology tool of claim 11, wherein the measurement unit is further configured to carry out the repeated measuring for a plurality of phases as the relations between the zeroth and the first order diffraction signals.

19. The metrology tool of claim 18, further comprising an optical phase scanner configured to carry out the repeated phase measurements.

20. The metrology tool of claim 11, further configured to identify, during a training stage, and remove inaccuracy-introducing illumination points.

21. The metrology tool of claim 11, wherein the measurement unit is further configured to carry out the repeated measuring for a plurality of angles and/or phases and/or wavelengths of the illumination to modify the relations between the zeroth and the first order diffraction signals.

22. The metrology tool of claim 18, further comprising a beam displacer configured to modify an illumination beam incidence angle between the repeated measurements.

23. The metrology tool of claim 11, wherein the illumination is annular and the diffractive target comprises at least two periodic structures having at least two corresponding different pitches, and wherein a width of the annular illumination and the pitches are selected to separate overlap regions between the zeroth order diffraction signal and each of the first order diffraction signals from each of the respective periodic structures.

* * * * *